United States Patent [19]
Martens

[11] Patent Number: 5,612,988
[45] Date of Patent: Mar. 18, 1997

[54] DEVICE FOR MEASURING THE MOMENTUM TRANSFER SPECTRUM OF X-RAY QUANTA ELASTICALLY SCATTERED IN AN EXAMINATION ZONE

[75] Inventor: Gerhard Martens, Henstedt-Ulzburg, Germany

[73] Assignee: U.S. Philips Corporation, New York, N.Y.

[21] Appl. No.: 601,408

[22] Filed: Feb. 14, 1996

[30] Foreign Application Priority Data

Feb. 15, 1995 [DE] Germany .................. 195 04 952.7

[51] Int. Cl.[6] ................................................. G01N 23/201
[52] U.S. Cl. ........................................... 378/86; 378/98.4
[58] Field of Search ...................................... 378/86, 98.4

[56] References Cited

U.S. PATENT DOCUMENTS 5,231,652  7/1993  Harding .................... 378/86
5,265,144  11/1993 Harding et al. ............. 378/86
5,394,453  2/1995  Harding .................... 378/86

Primary Examiner—Michael J. Tokar
Assistant Examiner—David Vernon Bruce
Attorney, Agent, or Firm—Michael Balconi-Lamica

[57] ABSTRACT

The invention relates to a device for measuring the momentum transfer spectrum of X-ray quanta elastically scattered in an examination zone, comprising an X-ray source and a detector device with a plurality of detector elements, one of which serves to measure a reference radiation beam. Attractive results are obtained in that between the examination zone and the X-ray source there is arranged at least one scatter member which scatters the X-rays emitted by the X-ray source, the reference radiation beam being formed from the part of the scattered radiation which reaches the reference detector element rectilinearly through the examination zone.

10 Claims, 2 Drawing Sheets

DEVICE FOR MEASURING THE MOMENTUM TRANSFER SPECTRUM OF X-RAY QUANTA ELASTICALLY SCATTERED IN AN EXAMINATION ZONE

BACKGROUND OF THE INVENTION

1. Field of the Invention

The invention relates to a device for measuring the momentum transfer spectrum of X-ray quanta elastically scattered in an examination zone, comprising an X-ray source, a primary diaphragm device which is arranged between the X-ray source and the examination zone in order to form a primary beam which traverses the examination zone as the surface of a cone and wherefrom the elastically scattered X-ray quanta to be measured emanate, and to form a reference radiation beam which emanates from the X-ray source and traverses the examination zone, a detector device for detecting X-ray quanta from the examination zone, comprising a plurality of detector elements for measuring elastic scattered radiation from the examination zone and at least one reference detector element on which the reference radiation beam is incident.

2. Discussion of the Related Art

A device as disclosed in EP-OS 556 887 (=U.S. Ser. No. 015096) serves to determine the momentum transfer spectrum of elastically scattered X-ray quanta. The momentum transfer spectra associated with the various layers of the examination zone contain information concerning the crystallographic structure of the material present in these layers. Therefore, they can be used, like a finger print, for the identification of substances present in the examination zone, for example for the inspecting luggage for the presence of, for example explosives.

The attenuation of the X-rays, both before and after the scattering by an object present in the examination zone represents a drawback of this system. It is dependent on the one hand on the energy of the X-rays to be detected and on the other hand on the type and distribution of attenuating material in the examination zone. In order to enable correction for such attenuation, the similarly attenuated reference radiation beam is detected by the reference detector element.

The reference radiation in the known device is produced by a pencil beam whose position in space is given by the connecting line between the focus of the X-ray source and the center of the detector device. It is a drawback that the intensity of the pencil beam is substantially higher than the intensity of the elastically scattered X-rays measured by the detector device. In order to prevent saturation of the reference detector element by the reference radiation during a measurement, either the cross-section of the pencil beam must be very small (only a few square micrometers) or the pencil beam must be substantially attenuated by an absorber, the effect of the attenuation on low-energy X-ray quanta then being stronger than that on high-energy X-ray quanta. It is another drawback of the known device that the pencil beam traverses a part of the examination zone other than that traversed by the conical primary radiation beam and the X-ray quanta elastically scattered therein. If the material is not sufficiently homogeneously distributed across the examination zone, errors will thus occur in the attenuation correction.

SUMMARY OF THE INVENTION

It is an object of the present invention to provide a device of the kind set forth in which the generating of the reference radiation is improved. This object is achieved in accordance with the invention in that at least one scatter body is arranged between the examination zone and the X-ray source in order to scatter the X-rays emanating from the X-ray source, and that the reference radiation beam is formed from the part of the scattered radiation which reaches the reference detector element rectilinearly through the examination zone.

Thus, in conformity with the invention the reference radiation is formed exclusively by the scattered radiation emanating from the scatter body (bodies) and not by X-rays reaching the reference detector element from the X-ray source via a straight path. As a result, the intensity of the reference radiation approximates the intensity of the elastically scattered radiation. Moreover, the part of the examination zone traversed by the reference radiation better matches the part traversed by the elastically scattered X-ray quanta to be measured, notably if the scatter body is arranged outside the volume enclosed by the conical primary radiation beam.

In a further embodiment of the invention, the scatter body consists of an amorphous material which exhibits a wideband scatter spectrum in the energy range of the X-ray quanta emitted by the X-ray source. Discontinuities which could occur in the scatter spectrum if the scatter body were made of a material having a crystalline structure are thus avoided. The scatter body should not excessively attenuate the X-rays, i.e. it should not contain materials of an atomic number higher than 13 or only a small concentration thereof.

It has been found that it is particularly attractive if the scatter body consists of polymethyl methacrylate (PMMA). PMMA, being known as PLEXIGLAS, is an amorphous scatter material having a low X-ray absorption and a wideband spectrum.

In a further embodiment of the invention the scatter body is arranged so that therein the X-ray quanta are scattered mainly elastically to the reference detector element. Thus, the reference radiation then also consists mainly of elastically scattered X-ray quanta. In a further embodiment of the invention the mean scatter angle of the X-ray quanta scattered to the reference detector element by the scatter body amounts to approximately 0.05 rad. A PLEXIGLASS scatter body has a wide scatter range of from 30 to 130 keV for such a mean scatter angle if the X-rays are generated by an X-ray tube with an tube voltage of 160 kV, scattering then being particularly intense in the range from 35 to 60 keV. This is attractive because the intensity of the radiation in this energy range is attenuated more than that in the energy range therebeyond.

A preferred embodiment comprises two scatter bodies which are symmetrically arranged relative to a system axis interconnecting the X-ray source and the detector device. Two scatter bodies which are comparatively narrow in the direction perpendicular to the system axis suffice to produce the reference radiation of the necessary intensity, and enable easy formation of a reference radiation beam. For the purpose of beam forming in a further embodiment the primary diaphragm device is provided with a slit which extends parallel to a plane containing the system axis and the scatter bodies.

In another embodiment means are provided for displacing an object to be examined and the examination zone relative to one another, the direction of displacement being perpendicular to a plane in which the system axis and the two scatter members are situated. It is thus achieved that upon relative displacement the reference beam traverses essentially the same part of the examination zone as the elastically scattered X-rays to be measured.

Further embodiments of the invention are described in the dependent claims.

These and other aspects of the invention will be apparent from and elucidated with reference to the embodiments described hereinafter.

DETAILED DESCRIPTION OF THE PREFERRED EMBODIMENTS

Figure 1:
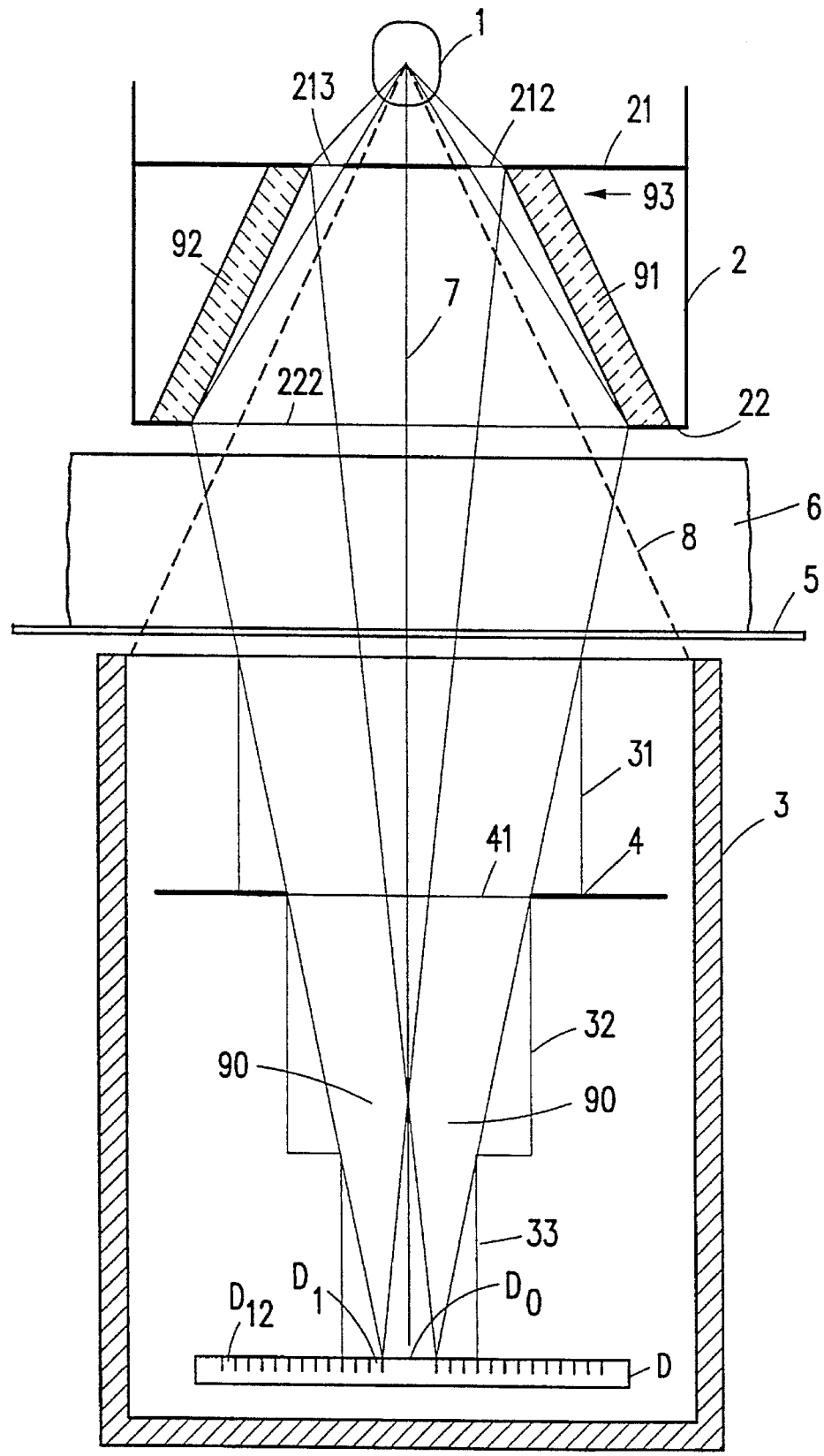
FIG. 1 shows a device in accordance with the invention.

The embodiment of FIG. 1 is not shown to scale. In comparison with the dimensions in the vertical direction, the dimensions in the horizontal direction have been enlarged by approximately a factor 10. The device comprises an X-ray source 1, a primary diaphragm device 2 and a housing 3 which accommodates a secondary diaphragm device 4 and a detector device D. Between the primary diaphragm device 2 and the housing 3 there is arranged a conveyor belt 5 which is capable of transporting an object 6 to be examined, for example a piece of luggage, in the direction perpendicular to the plane of drawing of FIG. 1. Moreover, the examination device and the object 6 can be displaced horizontally with respect to one another so that all parts of the object (only partly shown in FIG. 1), can be successively examined in a meandering scanning motion.

The examination device is essentially constructed so as to be rotationally symmetrical with respect to a system axis 7 which connects the center of the circular detector device D to the focus of the X-ray source 1 wherefrom the X-rays emanate. The X-ray source is preferably formed by an X-ray tube in the focus of which polychromatic X-rays (Bremsstrahlung) are generated by electron bombardment. At a tube voltage of, for example 150 kV such an X-ray robe can emit high-intensity X-ray quanta at in the energy range of between 30 kV and 120 keV. The X-rays first pass through the primary diaphragm device 2 which comprises a first diaphragm plate 21 at its side which faces the X-ray source and a second diaphragm plate 22 at its side which is remote from the X-ray source. The diaphragm plates 21 and 22 extend perpendicularly and concentrically with respect to the system axis 7.

Figure 2:
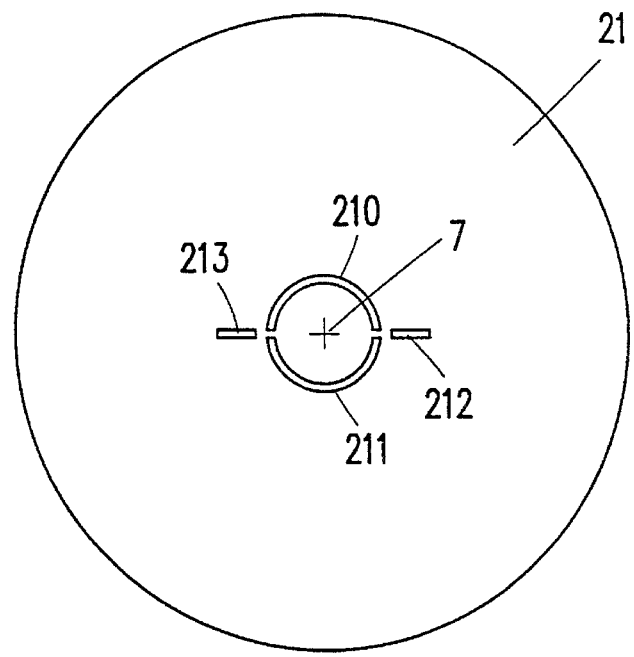
FIG. 2 shows a first part of the primary diaphragm device provided therein.
Figure 3:
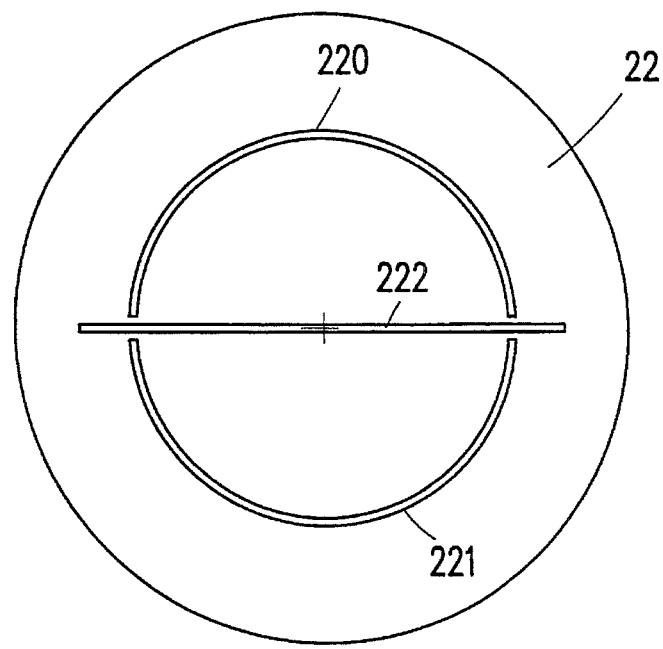
FIG. 3 shows a second part of said primary diaphragm device.

FIG. 2 is a plan view of the diaphragm plate 21. It comprises two semicircular slits 210 and 211 which are concentric with the system axis. The diaphragm plate 22 shown in FIG. 3 also comprises two semicircular slits 220 and 221 which are concentric with the system axis 7 but whose diameter is larger, so that the slits 210, 211 and 220, 221 in the diaphragm plates 21 and 22 form a primary radiation beam 8 (denoted by dashed lines in FIG. 1) from the X-rays produced by the X-ray source 1, said primary radiation beam traversing the examination zone along the surface of a cone, preferably a cone having a circular cross-section.

The X-ray quanta of the primary radiation beam 8 may be scattered in an examination zone defined by the space between the diaphragm plate 22 and the conveyor belt 5 and containing the object 6 to be examined. The scattered X-ray quanta are detected by the detector device D which comprises, in addition to a central detector element $D_0$, further detector elements $D_1 \ldots D_{12}$ which enclose the central detector $D_0$ in the form of rings or in the form of segments of such rings. Considering the given geometry of the examination device, the detector device is reached exclusively by X-ray quanta which have been scattered in the examination zone at a scatter angle (being the angle wherethrough an X-ray quantum is deflected from its direction during a scattering process) of no more than 4° (0.07 rad). In the case of the above-mentioned energy of the X-ray quanta, mainly elastically scattered X-ray quanta are present in this angular range. The momentum transfer spectrum of elastically scattered X-ray quanta, i.e. the number of X-ray quanta as a function of the momentum transfer, contains information as regards the structure of the scattering material in the examination zone so that it can be used, like a finger print, for identifying the material present in the object 6 to be examined.

The momentum transfer is at least approximately proportional to the product of the energy of the elastically scattered (without energy loss) X-ray quanta and the scatter angle. The energy of the X-ray quanta can be measured by the detector device D. The scatter angle must be given by the secondary diaphragm device 4 in such a manner that each detector element $D_1 \ldots D_{12}$ can receive scattered radiation only from a given layer of the examination zone and only at a given scatter angle or at an angle situated in a small range around said scatter angle. To this end, the diaphragm device 4 comprises at least one flat diaphragm plate which comprises a plurality of annular diaphragm apertures which are not shown in the drawing. Via one of these apertures, each detector element $D_1 \ldots D_{12}$ can "see" a part of the examination zone traversed by the primary radiation beam 8.

The examination device described thus far is known from EP-OS 556 887 (=U.S. Ser. No. 15 096); reference is made explicitly thereto for further details.

The signals measured by the detector elements $D_1 \ldots D_{12}$ are dependent not only on the momentum transfer spectrum of the scattering material, but also on the attenuation of the primary radiation beam and the scattered radiation in the examination zone as well as on the intensity of the X-rays emitted by the X-ray source. In order to eliminate these influences, the known examination device utilizes a further detector element to measure a reference radiation beam which is also dependent on the attenuation in the examination zone and on the intensity of the X-ray source, but not on the momentum transfer spectrum of the scattering material. In the known device this reference radiation beam is formed by a primary beam whose position is coincident with the system axis 7, thus causing the described drawbacks.

In accordance with the invention, the reference radiation is derived from the X-rays emitted by the X-ray source via a scatter body which is arranged between the examination zone and the X-ray source, preferably inside the primary diaphragm device. The scatter body may be shaped so as to be rotationally symmetrical with respect to the system axis 7. However, because only some segments thereof are required, it is advantageous to utilize two scatter members 91 and 92 which are symmetrically arranged relative to the system axis 7 and which have a small thickness of a few millimeters in the direction perpendicular to the plane of drawing. The scatter bodies 91 and 92 are situated outside the volume enclosed by the primary radiation beam 8 and define a plane (or a slice because of their dimension in the direction perpendicular to the plane of drawing) which is perpendicular to the transport direction of the belt 5.

The X-rays produced by the X-ray source 1 are incident on the scatter bodies 91 and 92, via slits 212 and 213 (FIG. 2) in the diaphragm plate 21 which are situated so as to be mirror-symmetrical with respect to the system axis 7, and produce scattered radiation therein. The scattered radiation emanates from an elongate slit 222 (see FIG. 3), extending parallel to the plane of drawing and provided in the diaphragm plate 22, and forms a reference radiation beam which is incident on the central detector element $D_0$, after having traversed the examination zone, only a strip parallel to the slit 222 of said detector element being struck. Diaphragm plates 31, 32 and 33 in the housing 3, arranged in front of and behind the reference radiation beam 90, ensure that the reference radiation beam does not expand in the direction perpendicular to the plane of drawing and strip-shaped covers for the detector elements $D_1 \ldots D_{12}$ (not shown) can prevent these elements from being struck by said reference radiation beam. A slit 41 in the secondary diaphragm device 4 allows passage of the reference radiation beam, the previously mentioned annular imaging slits possible being interrupted by the slit 41.

The energy spectrum of the X-ray quanta scattered in the scatter members 91 and 92 is dependent not only on the energy spectrum of the X-ray source, but also on the energy dependency of the scatter cross-section of the material constituting the scatter members, and on the scatter angle at which the X-ray quanta are scattered in the scatter members 91, 92. The mean scatter angle amounts to approximately 0.05 rad so that the reference radiation beam contains mainly elastically scattered X-rays. In the case of elastically scattered radiation, however, very pronounced peaks of the energy dependency of the scatter cross-section could occur if the scatter bodies were to have a crystalline structure. Therefore, the scatter bodies should consist of an amorphous material having a wideband scatter spectrum in the energy range of the X-ray quanta emitted by the X-ray source and for the given scatter angle, i.e. a monotonously varying energy dependency of the scatter cross-section.

Water would be a suitable material, but it is not readily possible to form a scatter body therefrom, unless it is formed as a hydrogenous gelatine provided on the surface of a carrier body or the like. Among the synthetic materials PVC is absolutely amorphous and it also causes wideband scattering like water; however, it has the drawback that, due to its chloride content, the transparency of PVC to X-rays is less than optimum.

It has been found that plexiglass (polymethyl methacrylate or PMMA) is a particularly suitable material for the scatter bodies. The X-ray quanta elastically scattered therein at a scatter angle of 0.05 rad are also scattered in a wide energy range, the scatter cross-section exhibits a maximum in the energy range of from 35 to 60 KeV, but decreases appreciably for higher quantum energies. This is an advantage because X-ray quanta in this energy range are strongly absorbed by the material in the examination zone in comparison with X-ray quanta with a higher energy.

It may be useful to arrange the upper part of the scatter bodies so as to be pivotable about their base so that the distance between the area of the scatter body nearest to the X-ray source and the system axis 7 is adjustable. To this end, this area may be displaceable in conformity with the arrow 93, for example by means of a micrometer screw. The further this area is displaced inwards, the less X-rays will be incident on the scatter body and the lower the intensity of the scattered radiation produced therein will be. On the other hand, in the case of such a displacement the mean scatter angle also changes, so that such an adjustment is accompanied by a variation of the spectral distribution of the reference radiation. Therefore, this area should be adjusted so that a compromise is reached between the intensity of the scattered radiation and the desired spectral distribution.

EP-OS 496 454 (=U.S. Pat. No. 5,265,144) describes how the momentum transfer spectrum can be determined from the signals acquired by the detector device. A similar approach could be used for the invention. However, even better results are obtained if the measured results acquired by means of the detector elements $D_0$ as well as $D_1 \ldots D_{12}$ are related to the measured results obtained by means of the same detector elements if instead of the object to be examined a calibration object having exactly known scatter properties is arranged in the beam path. The measurements performed on the object to be examined should then be related to the measurements performed on the calibration object.

For the purpose of illustration it is assumed that in the presence of the calibration object a detector element, for example $D_{12}$, produces, after the processing by a pulse height analyzer as described in EP-OS 496 445 a series of numbers I'(E), said series indicating the number of X-ray quanta incident in a number of locations as a function of the energy. Said series represents the energy spectrum of the X-ray quanta scattered in the calibration object (within the layer assigned to $D_{12}$). The series of numbers supplied by the same detector element, in conjunction with the downstream electronics, when the object 6 to be examined is present in the examination zone is referred to as I(E). A quotient a(E) is then obtained as follows:

$$\frac{I(E)}{I'(E)} = a(E) \quad (1)$$

Therein, a(E) is also a series of numbers whose respective values are produced by dividing the number of X-ray quanta detected by the relevant detector element for a given energy range, for example from 50 keV to 50.1 keV, in the presence of the object 6 to be examined in the examination zone by the number of X-ray quanta detected by the same detector element in the same energy range when the calibration object is present in the examination zone.

Analogously, during the two measurements the detector element $D_0$, detecting the reference radiation beam, produces corresponding series of numbers which are denoted as R(E) and R'(E). Therefrom, a series of numbers b(E) can be determined as $$\frac{R(E)}{R'(E)} = b(E) \quad (2)$$

From the values a(E) and b(E) there can be determined a (twice) normalized energy spectrum S(E) of the material which is present in the part of the object to be examined wherefrom scattered radiation can strike the relevant detector element. It holds that:

$$\frac{a(E)}{b(E)} = \frac{S(E)}{(S'(E)} \quad (3)$$

Therein, S'(E) is the (known) normalized energy spectrum of the material constituting the calibration member. The momentum transfer spectrum may be derived from the energy spectrum S(E) by multiplying the energy scale by a constant corresponding to the half of the sine of the scatter angle (assigned to $D_{12}$).

I claim:
1. A device for measuring a momentum transfer spectrum of X-ray quanta elastically scattered in an examination zone, comprising:
    an X-ray source;

a primary diaphragm device arranged between said X-ray source and the examination zone for forming a primary radiation beam which traverses the examination zone as a surface of a cone and wherefrom the elastically scattered X-ray quanta to be measured emanate, said primary diaphragm device further for forming a reference radiation beam which emanates from the X-ray source and traverses the examination zone;

a detector device for detecting X-ray quanta emanated from the examination zone, wherein said detector device comprises a plurality of detector elements for measuring elastic scattered radiation from the examination zone and at least one reference detector element on which the reference radiation beam is incident; and at least one scatter member arranged between the examination zone and said X-ray source in order to scatter X-rays emanating from said X-ray source, and wherein the reference radiation beam is formed from a part of the scattered radiation which reaches the reference detector element rectilinearly through the examination zone.

2. The device as claimed in claim 1, wherein said at least one scatter member comprises an amorphous material which exhibits a wideband scatter spectrum in an energy range of the X-ray quanta emitted by said X-ray source.

3. The device as claimed in claim 2, wherein said at least one scatter member further comprises polymethyl methacrylate (PMMA).

4. The device as claimed in claim 2, further wherein said at least one scatter member is arranged so that therein X-ray quanta are scattered mainly elastically to the reference detector element.

5. The device as claimed in claim 4, a mean scatter angle of the X-ray quanta scattered to the reference detector element by said at least one scatter member amounts to approximately 0.05 rad.

6. The device as claimed in claim 1, wherein said at least one scatter member comprises two scatter members which are mutually offset 180° relative to a system axis interconnecting said X-ray source and said detector device.

7. The device as claimed in claim 6, further wherein said primary diaphragm device is provided with a slit which extends parallel to a plane containing the system axis and the two scatter members.

8. The device as claimed in claim 6, further comprising means for displacing an object to be examined and the examination zone relative to one another in a direction of displacement perpendicular to a plane in which the system axis and the two scatter members are situated.

9. The device as claimed in claim 1, wherein a distance between an area of said at least one scatter member nearest to said X-ray source and a system axis is adjustable, wherein the system axis comprises an axis interconnecting said x-ray source and said detector device.

10. The device as claimed in claim 6, further comprising plates of an X-ray absorbing material provided between the examination zone and said detector device, said plated further being provided to both sides of and parallel to a plane in which the system axis and the two scatter members are situated.

\* \* \* \* \*